United States Patent
Farooq et al.

(10) Patent No.: US 11,986,309 B2
(45) Date of Patent: May 21, 2024

(54) PASSENGER IDENTIFICATION AND PROFILE MAPPING VIA BRAINWAVE MONITORING

(71) Applicant: TOYOTA MOTOR ENGINEERING & MANUFACTURING NORTH AMERICA, INC., Plano, TX (US)

(72) Inventors: Muhamed K. Farooq, Ann Arbor, MI (US); Chungchih Chou, Ann Arbor, MI (US); Sean P. Rodrigues, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 501 days.

(21) Appl. No.: 17/226,713

(22) Filed: Apr. 9, 2021

(65) Prior Publication Data
US 2022/0322994 A1    Oct. 13, 2022

(51) Int. Cl.
| A61B 5/38 | (2021.01) |
| A61B 5/00 | (2006.01) |
| A61B 5/11 | (2006.01) |
| A61B 5/18 | (2006.01) |
| A61B 5/384 | (2021.01) |

(52) U.S. Cl.
CPC ............ *A61B 5/384* (2021.01); *A61B 5/112* (2013.01); *A61B 5/18* (2013.01); *A61B 5/7435* (2013.01)

(58) Field of Classification Search
CPC ........... A61B 5/112; A61B 5/117; A61B 5/18; A61B 5/372; A61B 5/384; A61B 5/7435; G06V 20/597; G06V 40/15; G06V 40/25
See application file for complete search history.

(56) References Cited

U.S. PATENT DOCUMENTS

| 9,809,169 | B1 * | 11/2017 | Naboulsi | B60R 1/025 |
| 10,019,060 | B2 | 7/2018 | Cash | |
| 10,786,209 | B2 * | 9/2020 | Park | A61B 5/389 |
| 11,091,168 | B2 * | 8/2021 | Chou | B60W 50/0098 |
| 2013/0201316 | A1 * | 8/2013 | Binder | H04L 67/12 |
| | | | | 701/2 |
| 2015/0338917 | A1 | 11/2015 | Steiner et al. | |
| 2017/0042439 | A1 * | 2/2017 | Yeow | G16H 10/60 |
| 2017/0091741 | A1 * | 3/2017 | Todeschini | A61B 5/369 |
| 2017/0305349 | A1 * | 10/2017 | Naboulsi | B60R 1/025 |

(Continued)

FOREIGN PATENT DOCUMENTS

| CN | 205302426 U | 6/2016 |
| KR | 10-2031958 B1 | 10/2019 |

(Continued)

*Primary Examiner* — Tyler J Lee
(74) *Attorney, Agent, or Firm* — Oblon, McClelland, Maier & Neustadt, L.L.P.

(57) ABSTRACT

The disclosure is related configuring a vehicle according to a user profile, where an individual user profile can be selected from a registry containing one or more user profiles using electroencephalogram (EEG). An additional biometric, such as gait, can also be used. The user profiles can include a variety of the user preferences, such as the preferred climate, seat settings, mode of payment, route to take, and more. A mobile device can also be used to add a layer of security and privacy, where the mobile device has sole access to the user's user profile.

20 Claims, 10 Drawing Sheets

(56) References Cited

U.S. PATENT DOCUMENTS

| | | | |
|---|---|---|---|
| 2017/0311831 A1 | 11/2017 | Freer et al. | |
| 2017/0313324 A1* | 11/2017 | Kumai | B60W 40/02 |
| 2019/0056731 A1* | 2/2019 | Westbrook | G05D 1/0214 |
| 2019/0159735 A1* | 5/2019 | Rundo | A61B 5/725 |
| 2019/0310707 A1* | 10/2019 | Hwang | G06F 3/015 |
| 2020/0172091 A1* | 6/2020 | Takasaki | G08G 1/0145 |
| 2020/0229730 A1* | 7/2020 | Wang | A61B 5/7278 |
| 2020/0247425 A1* | 8/2020 | Chou | A61B 5/245 |
| 2022/0230479 A1* | 7/2022 | Palaniappan | H04W 4/44 |

FOREIGN PATENT DOCUMENTS

| | | |
|---|---|---|
| KR | 10-2020-0035612 | 4/2020 |
| WO | 2005/004067 A1 | 1/2005 |
| WO | 2008/157544 A1 | 12/2008 |
| WO | 2017/189203 A1 | 11/2017 |

* cited by examiner

PASSENGER IDENTIFICATION AND PROFILE MAPPING VIA BRAINWAVE MONITORING

BACKGROUND

It is not uncommon for vehicles to be shared amongst multiple people, whether they are family members sharing a car, or strangers utilizing a car sharing service. Different users of a vehicle often have varying configuration preferences, such as the ideal internal temperature or seat configuration. Therefore, a vehicle that can recognize an individual and automatically configure itself to that particular user's preferences can be very desirable.

SUMMARY

The disclosure is related to a vehicle system comprising processing circuitry configured to collect electroencephalogram (EEG) data, using a brainwave detector, of a user, and in a case that the EEG data matches pre-stored EEG data in a registry, configure the vehicle according to a user profile in the registry corresponding to the pre-stored EEG data.

In one embodiment, the processing circuitry is further configured to transmit the EEG data to a mobile device, the mobile device having access to the registry and the user profile, and in the case that the EEG data of the user matches the pre-stored EEG data in the registry, receive the user profile corresponding to the pre-stored EEG data from the mobile device.

In one embodiment, the processing circuitry is further configured to display one or more icons to the user to generate the EEG data (i.e. the user's unique EEG signature).

In one embodiment, the brainwave detector is a contactless brainwave detector (CBD).

In one embodiment, the user profile include at least one of a desired destination, a routing preference, a desired temperature range, desired humidity range, desired light settings, desired audio settings, and desired seat settings for the vehicle. In one embodiment, the user profile includes payment information of the user.

In one embodiment, the brainwave detector is inside the vehicle. In another embodiment, the brainwave detector is disposed on an exterior of the vehicle.

The present disclosure is also related to a vehicle system comprising, processing circuitry configured to collect EEG data, using a brainwave detector, of a user, collect secondary biometric data of the user using one or more sensors, and in a case that at least one of the EEG data and the secondary biometric data match pre-stored EEG data and pre-stored secondary biometric data in a registry, configure the vehicle according to a user profile in the registry corresponding to the pre-stored EEG data and the pre-stored secondary biometric data.

In one embodiment, the secondary biometric data is gait data of the user's gait.

In one embodiment, the brainwave detector is a contactless brainwave detector.

The present disclosure is also related to a method comprising: collecting EEG data, using a brainwave detector, of a user; and in a case that the EEG data matches pre-stored EEG data in a registry, configuring a vehicle according to a user profile in the registry corresponding to the pre-stored EEG data.

One embodiment further comprises transmitting the EEG data from the vehicle to a mobile device, the mobile device having access to the registry and the user profile, and in the case that the EEG data of the user matches the pre-stored EEG data in the registry, transmitting the user profile corresponding to the pre-stored EEG data from the mobile device to the vehicle.

One embodiment further comprises displaying one or more icons to the user to generate the EEG data (i.e. the user's unique EEG signature).

One embodiment further comprises collecting secondary biometric data of the user.

In one embodiment, the brainwave detector is a contactless brainwave detector.

In one embodiment, wherein the user profile includes at least one of a desired destination, a routing preference, a desired temperature range, desired humidity range, desired light settings, desired audio settings, and desired seat settings for the vehicle. In one embodiment, the user profile includes payment information of the user.

In one embodiment, the brainwave detector is inside the vehicle. In another embodiment, the brainwave detector is disposed on an exterior of the vehicle.

DETAILED DESCRIPTION

One technique to identify an individual is by reading their brainwave activity. The readings of how a brain reacts to certain words or tasks are unique to each individual. Electroencephalogram (EEG) can be used to read brainwave activity. Although typically performed using electrodes placed on a person's head, EEG now has the capability to be performed contact-free.

Another technique capable of uniquely identifying individuals is by analyzing their gait. Gait is another biometric, as each individual has a unique gait. As was the case with performing EEG, gait can be analyzed contact-free.

The present disclosure is related to using brainwave detectors in a vehicle to obtain EEG data corresponding to a user, and attempting to match the obtained EEG data to pre-stored EEG data of a corresponding user profile stored in a registry. In one embodiment, the user can think of a predetermined thought process (i.e. password), such as a repetitive task, word, or phrase, to generate the EEG data. If the obtained EEG data matches the pre-stored EEG data, the corresponding user profile linked to the pre-stored EEG data is used to configure the vehicle. The brainwave detectors can be contactless brainwave detectors (CBDs) as discussed in detail below, or they can be contact-based brainwave detectors. For example, contact-based brainwave detectors may be embedded in a hat or similar item, and wirelessly communicate readings to another device, such as a receiver in a vehicle or a cell phone.

In another exemplary embodiment, another form of biometric data, such as gait data, can also be obtained. The obtained gait data and EEG data can be compared pre-stored EEG data and pre-stored gait data in the registry. According to one exemplary embodiment, if the EEG data and the gait data match to pre-stored EEG data and pre-stored gait data in the registry, the corresponding user profile is used to configure the vehicle. According to another exemplary embodiment, if the EEG data or the gait data match to pre-stored EEG data and pre-stored gait data in the registry, the corresponding user profile is used to configure the vehicle. It can be appreciated that additional or alternative biometrics can be used in other embodiments, such as facial recognition, fingerprints, finger geometry (the size and position of fingers), iris recognition, vein recognition, retina scanning, voice recognition, DNA (deoxyribonucleic acid) matching, digital signatures, smell, height, weight, and behavioral profiling.

The registry can include user profiles of users who have set up user profiles. The user profile can be stored in the registry and include specific information related to each user, such as their pre-stored EEG data, pre-stored gait data, additional pre-stored biometric data, a desired destination, favorited destinations, vehicle configuration settings (e.g. lighting, temperature, audio, seating), payment information, desired route to take (e.g. least distance, least time), and more. After such as user profile has been created for a specific user, each time EEG or gait data of that user is gathered, it can be matched to the pre-stored EEG and/or pre-stored gait data corresponding to the user's user profile. If there is a match, the vehicle can be automatically configured according to the user profile. Setting up the user profile and registry can involve conventional calibration techniques to build a database. For example, the EEG data may be collected as users are asked to look at posted images, signs, graphics, and icons to determine the brainwave response and to generate an EEG pattern that is unique to them so that the EEG data may be conditioned or normalized to enhance the system's ability to distinguish changes to the EEG data.

Figure 1A:
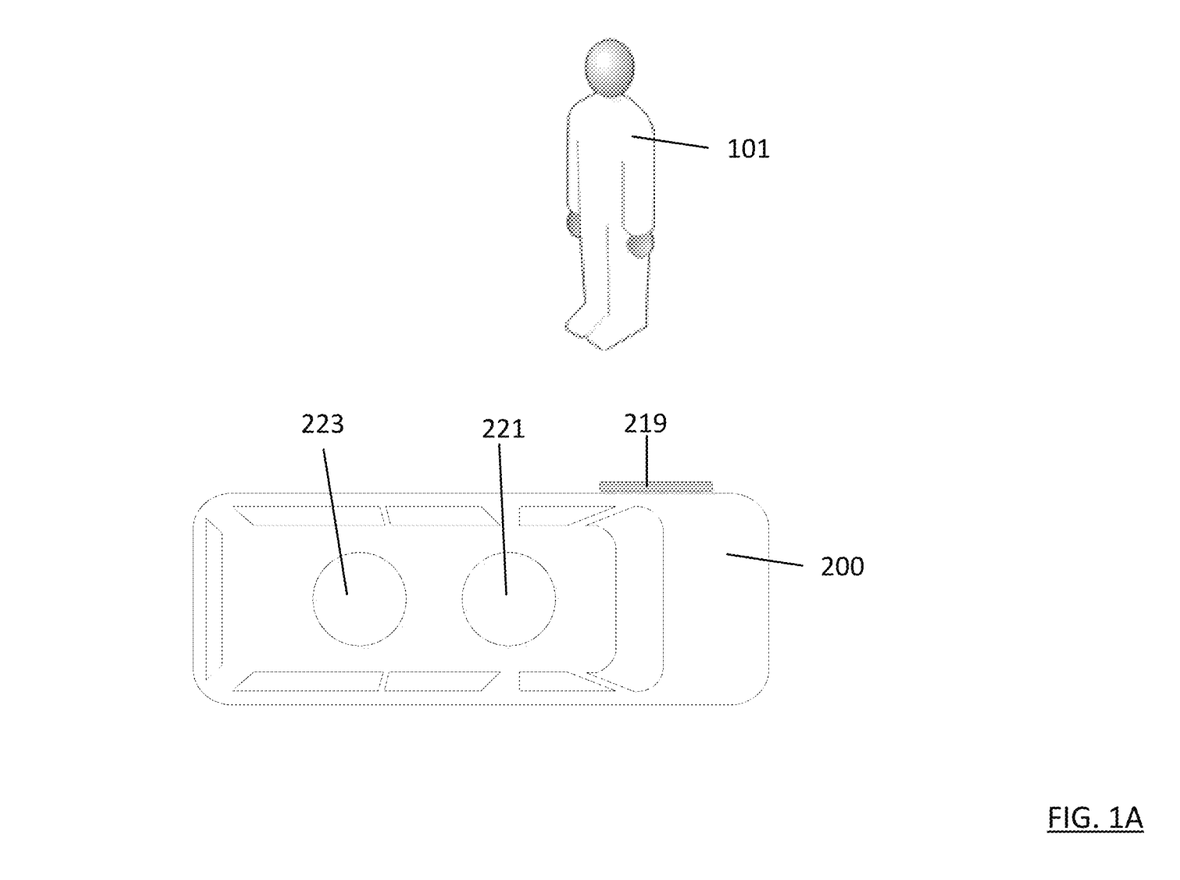
FIG. 1A illustrates a first scenario employing profile mapping, according to one embodiment of the present disclosure.

An exemplary scenario is shown in FIG. 1A. As a user 101 walks up to a locked vehicle 200, the gait sensor module 221 gathers gait data on the user's gait. Additionally, a CBD module 223 disposed on an exterior of the vehicle gathers EEG data from EEG brainwaves emitted by the user 101. In one embodiment, the user 101 is thinking a predefined thought process to reproduce EEG data matching the pre-stored EEG data in the registry, such as a particular phrase or image known by the user. In another embodiment, a display module 219 can be used to aid in generating EEG data. For example, one or more icons can be displayed on the display module 219 for the user 101 to view. Viewing these one or more icons can trigger visual evoked potential (VEP) responses in their user's 101 brain, which is captured as EEG data. Once the EEG data and gait data of the user 101 have been gathered, they are compared to pre-stored EEG data and pre-stored gait data in the registry. If the gathered EEG data and gait data match to pre-stored EEG data and pre-stored gait data of a user profile in the registry, the vehicle 200 is unlocked for the user 101 to enter, and configured according to the user's 101 user profile.

Figure 1B:
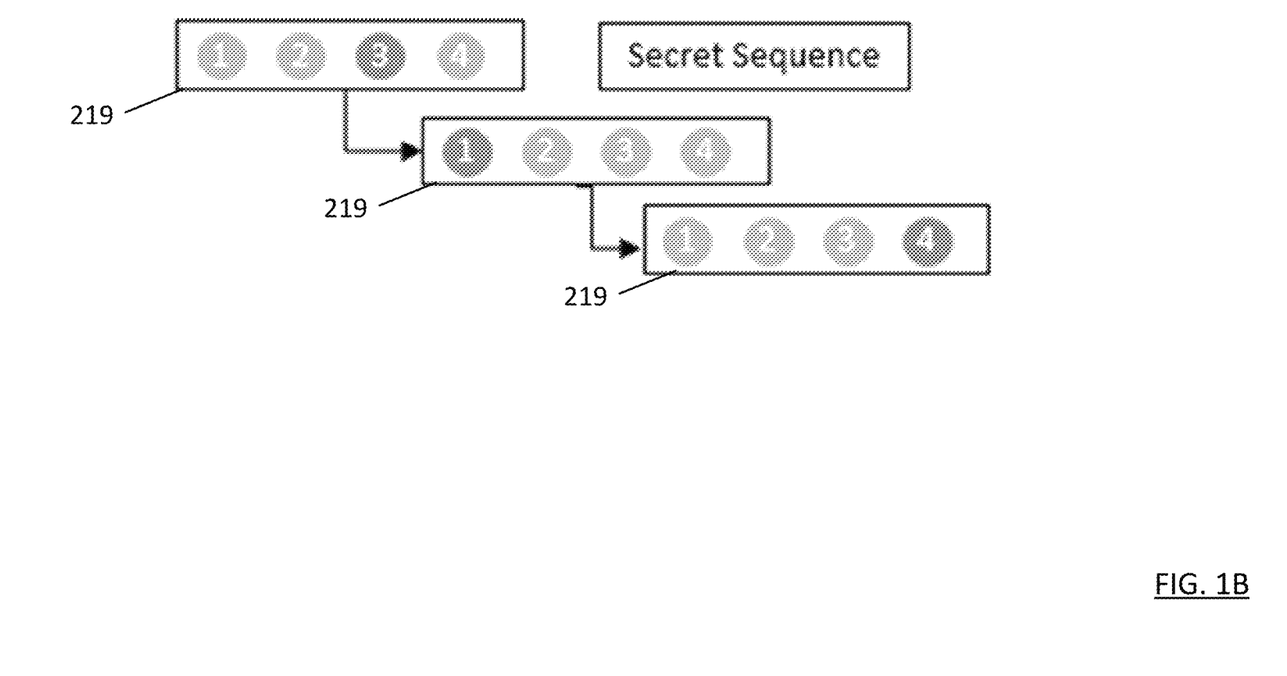
FIG. 1B illustrates viewing icons in a secret sequence to generate a particular brainwave pattern, according to one embodiment of the present disclosure.

In one embodiment, when the display module 219 is used for displaying icons, an additional layer of security can be added by having the user 101 look at a plurality of icons in a secret sequence. For example, as shown in FIG. 1B, four icons can be displayed in series on the display module 219, and the user 101 can know that they have to look at icons 3, 1, and 4 in sequence for their brain to generate the specific EEG data corresponding to the pre-stored EEG data linked to their user profile in the registry.

Figure 2:
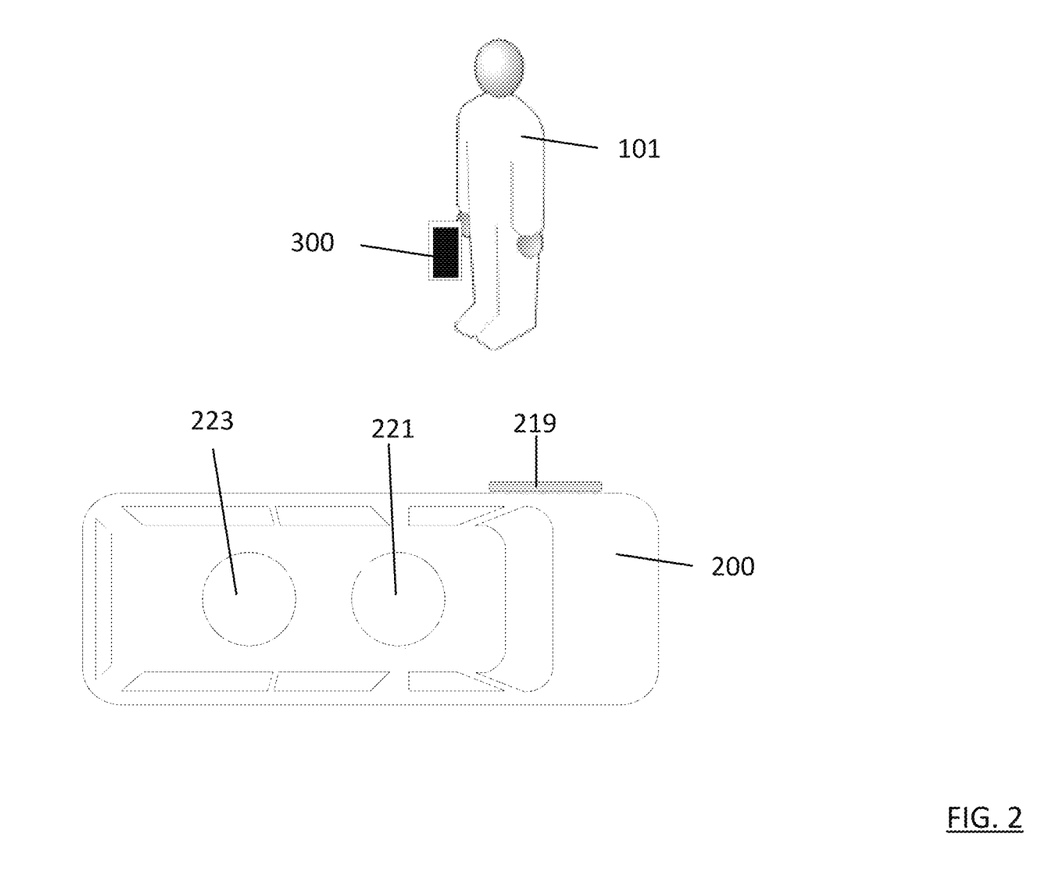
FIG. 2 illustrates a second scenario employing profile mapping, according to one embodiment of the present disclosure.

According to one embodiment, the registry can be accessed by the vehicle 200 directly, whether locally or via a network connection. In another embodiment, to add a layer of security and privacy, the registry can be accessible only by a separate device, such as a user's mobile device. This can be useful if a user does not want the vehicle 200 to have access to all of their profile information, or if a user wants to edit certain user profile information before sending it to the vehicle 200. For example, as shown in FIG. 2, as a user 101 walks up to a locked vehicle 200, the gait sensor module 221 gathers gait data on the user's gait, and a CBD module 223 disposed on an exterior of the vehicle gathers EEG data of EEG brainwaves emitted from the user 101. The gathered EEG data and gait data are then transmitted from the vehicle 200 to a mobile device 300, such as a phone, tablet, or smartwatch, having access to the user's 101 user profile information. If the EEG data and gait data received by the mobile device 300 match with the user's pre-stored EEG data and pre-stored gait data, the mobile device 300 sends the user's 101 user profile information to the vehicle 200. From there, the vehicle 200 can unlock for the user 101 and configure itself accordingly.

In another scenario, if the EEG data and gait data received by the mobile device 300 from the vehicle 200 match with the user's 101 pre-stored EEG data and pre-stored gait data, the mobile device 300 can display user profile information to the user 101 before it is sent to the vehicle 200. This can allow the user 101 to confirm their desire to configure the vehicle according to their user profile, as well as make edits to their user profile. For example, if there are multiple people nearby the vehicle 200 with user profiles stored in the registry, the user whose user profile will be used to configure the vehicle 200 can indicate this using their mobile device 300. In one instance, this can look like a notification pop-up on the mobile device 300 asking the user 101 if they want to configure the vehicle 200 according to their user profile.

Figure 3:
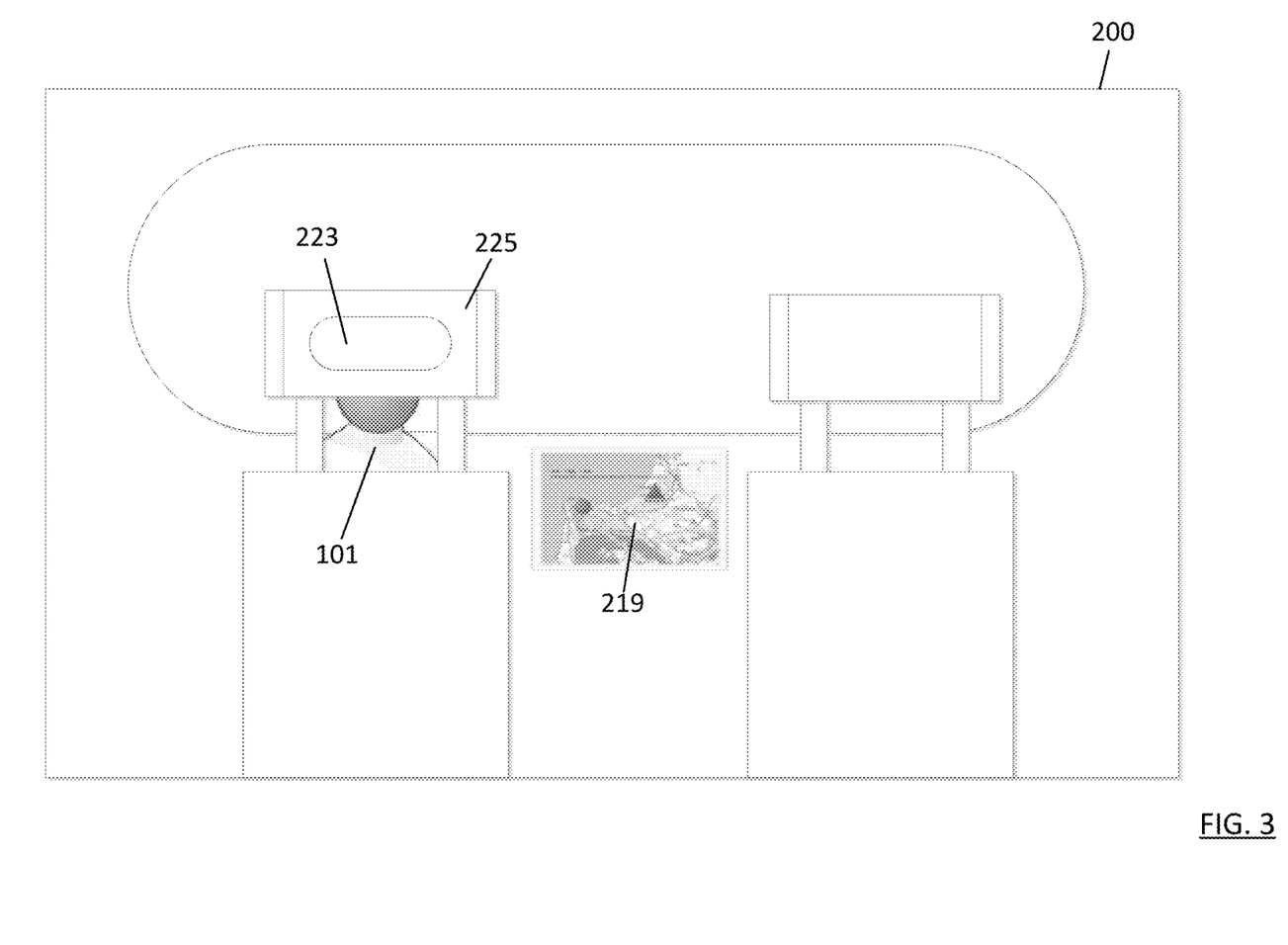
FIG. 3 illustrates a third scenario employing profile mapping, according to one embodiment of the present disclosure.

In one embodiment, rather than being placed on an exterior of the vehicle 200, the CBD module 223 can be placed inside the vehicle 200, such in a headrest or along the roof. For example, as shown in FIG. 3, a CBD module 223 is located in a headrest 225. EEG data of the user 101 is collected using the CBD module 223 when the user 101 sits in the vehicle 200. This EEG data can be used for retrieving the user's profile. Furthermore, the display module 219 can be located within the vehicle 200. In addition to displaying icons for generating EEG data by triggering VEP responses in the brain, the display module 219 can serve additional functionalities, such as displaying a list of possible destinations on a map using icons of varying frequencies, where the user can then generate additional EEG data indicating their desired destination. Placing the CBD module 223 inside the vehicle 200 can be useful if EEG data needs to be gathered for prolonged periods of time, since the user 101 will remain inside the vehicle 200 for the duration of the trip.

In one embodiment, if the user's 101 EEG data and/or gait data is not pre-stored in the registry, the vehicle 200 can lock, refuse to start, or disable certain features. In another embodiment, as previously mentioned, contact-based brainwave detectors can be used, such as an electrode cap. For example, as the user 101 enters the vehicle 200, they can wear an electrode cap for monitoring and recording EEG data.

In one embodiment, the user profile can include payment information, such as debit or credit card information. For example, if the vehicle 200 is a taxi or car sharing vehicle, the fare can be paid using the payment information.

In one embodiment, a user 101 can have multiple user profiles. For example, a user can think of a first password if they want to configure the vehicle 200 according to a first user profile, or the user can think of a second password if they want to configure the vehicle 200 according to a second user profile.

In one embodiment, the mobile device 300 can serve to keep the EEG profile of the user 101 updated by incrementally learning how their EEG signatures change over time. This can be useful for keeping the user's 101 user profile up to date if the user's 101 EEG response changes over time. In one embodiment, this learning can be performed using a machine learning-based technique.

It can be appreciated by one of skill in the art that the present disclosure can be viewed as a system. In one embodiment, the system comprises processing circuitry configured to collect EEG data, using a brainwave detector, of a user; and in a case that the EEG data matches pre-stored EEG data in a registry, configure the vehicle according to a user profile in the registry corresponding to the pre-stored EEG data. In another embodiment, the system comprises processing circuitry configured to collect EEG data, using a brainwave detector, of a user; collect secondary biometric data of the user using one or more sensors; and in a case that at least one of the EEG data and the secondary biometric data match pre-stored EEG data and pre-stored secondary biometric data in a registry, configure the vehicle according to a user profile in the registry corresponding to the pre-stored EEG data and the pre-stored secondary biometric data.

Figure 4:
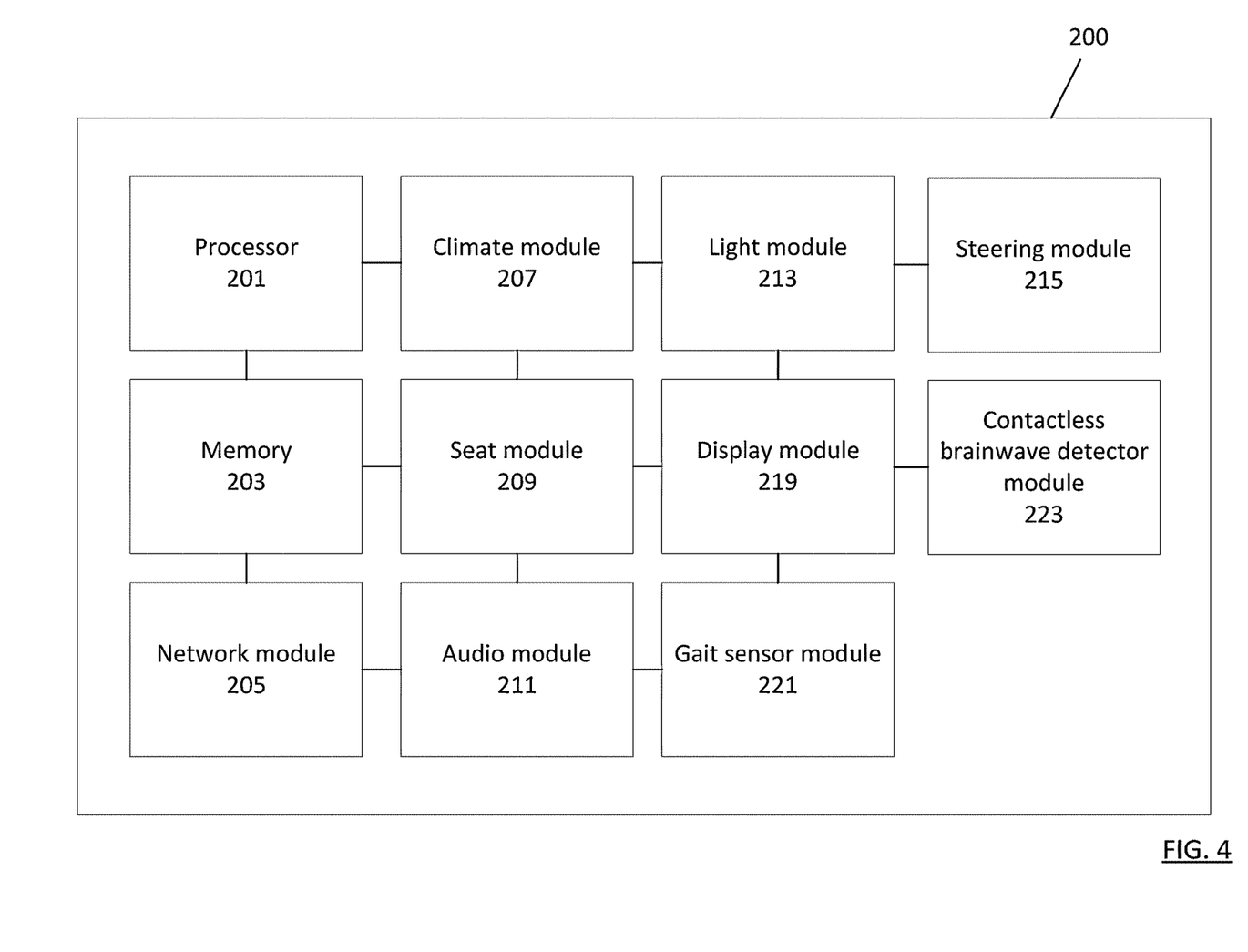
FIG. 4 is a hardware diagram of a vehicle, according to one embodiment of the present disclosure.

Referring to FIG. 4, the vehicle 200 can contain units for a processor 201, memory 203, network module 205, climate module 207, seat module 209, audio module 211, light module 213, steering module 215, contactless brainwave detector module 223, display module 219, and gait sensor module 221, according to an exemplary embodiment. The vehicle 200 can take up a myriad of forms, such as an autonomous car, manually driven car, bus, tram, trolley, boat, or airplane.

The processor 201 may be based on a reduced instruction set (RISC) circuit architecture, Von Neumann architecture, Harvard architecture, or any other processing circuit architecture that is known. The processor 201 may also be implemented as a system on a chip, application specific integrated circuit (ASIC), field programmable gate array (FPGA), or with discrete logic circuit components. The processor 201 may also be implemented in software that is executed on processing circuitry having any of the architectures described above. The processor 201 can be connected to and control to the memory 203, network module 205, climate module 207, seat module 209, audio module 211, light module 213, steering module 215, CBD module 223, display module 219, and gait sensor module 221. The processor 201 can be configured to run all or portions of method 600, 700, 800, and 900, discussed later herein.

The memory 203 can be used to store instructions and other data (e.g. registry of user profiles) needed by the processor 201 in order to carry out various tasks in accordance with exemplary aspects of the present disclosure. The memory 203 may include permanent instructions that do not require changes, such as lower-level routines. The memory 203 may include a combination of random access memory and erasable programmable read only memory (EPROM) in order to store programming instructions that may be periodically updated and data that may change periodically or frequently during as the processor 201 executes instructions.

The vehicle 200 can also include a network module 205, such as an Intel Ethernet PRO network interface card from Intel Corporation of America, for interfacing with a network. As can be appreciated, the network can be a public network, such as the Internet, or a private network such as an LAN or WAN network, or any combination thereof and can also include PSTN or ISDN sub-networks. The network can be wired, such as via an Ethernet network, or can be wireless, such as via a cellular network including EDGE, 3G, 4G, and 5G wireless cellular systems. The wireless network can also be Wi-Fi, Bluetooth, near-field communication (NFC), radio frequency identification device, or any other wireless form of communication that is known.

The climate module 207 can be used to control climate in the vehicle according to a user's user profile, such as a desired temperature range or desired humidity range. The climate module can include a temperature sensor, humidity sensor, air conditioning unit, and air quality sensor. For instance, if it is 75 degrees Fahrenheit in the vehicle but an incoming user's profile indicates a desired temperature of 70 degrees Fahrenheit, the processor 201 can command the climate module 207 to turn on an air conditioning unit until the temperature in the vehicle reaches 70 degrees Fahrenheit.

The seat module 209 can be used to control the seats of the vehicle according to a user's user profile. The seat module 209 can include seats, mechanisms to reorient the seats, a heating unit for the seats, headrests, and seatbelts. For example, if a user's profile indicates they want a heated seat that is elevated 12 inches above the floor, the processor 201 can command the seat module 209 to create those particular settings.

The audio module 211 can be used to control the audio of the vehicle 200 according to a user's user profile. The audio module 211 can include speakers and a radio. For instance, if the user's profile indicates that the user prefers a particular music genre or radio channel, the processor 201 can command the audio module 211 to create those particular settings.

The light module 213 can be used to control lighting in the vehicle 200 according to a user's user profile. The light module 213 can include lightbulbs. For instance, if a user's profile indicates they prefer a brightly lit environment, the lightbulbs can be fully turned on.

The steering module 215 can be used to control driving of the vehicle 200 to a desired destination according to a user's user profile. In addition, the vehicle 200 can be steered to a desired destination using different routes according to a user's routing preference, such as taking the route that is the fastest, shortest distance, avoids the highway, passes through certain points-of-interest, and so on.

The display module 219 can be an LCD display, CRT display, plasma display, OLED, LED or any other display known in the art. The display module 219 can also have speakers for emitting audio. The display module 219 can be placed in various locations, such as inside the vehicle 200 or on an exterior of the vehicle 200. The display module 219 can receive input from a user via touch. The display module 219 can be used to display information to a user, such as instructions or icons at varying frequencies for generating EEG data. Because different users will generate different EEG data even though the same icon is viewed, the icons can represent the user's password. The icons can be a particular pattern, word, image, and the like. Because a user's EEG data needs to be pre-stored, the same icons used to generate the pre-stored EEG data can be displayed back to the user via the display module 219.

The gait sensor module 221 can include one or more sensors for monitoring a user's gait. The one or more sensors can include a distance sensor (e.g. IR, LIDAR) or imaging sensor (e.g. camera). The gathered gait data can be compared to pre-stored gait data in the registry to determine whether a particular user is in the registry.

The contactless brainwave detector (CBD) module 223 can include one or more CBDs for wirelessly obtaining EEG data. Any contact-free method for collecting brainwave activity can be used. In one embodiment, the CBDs can use Neurobiomonitoring to collect the EEG data. The CBDs can be placed on the vehicle 200 in a myriad of ways, such as inside one or more headrests, along the sides of the vehicle 200, inside on the roof of the vehicle 200, outside on the roof of the vehicle 200, on a steering wheel, or any combination thereof. As can be appreciated, the CBD module 223 can be replaced with or supplemented by a contact-based brainwave detector module in one embodiment.

In other embodiments, the vehicle 200 can include additional components, such as additional sensors, for sensing additional biometrics. For example, a fingerprint sensor can be placed on the outside door handle of the vehicle 200 for gathering a user's fingerprint to compare to pre-stored fingerprint data.

Figure 5:
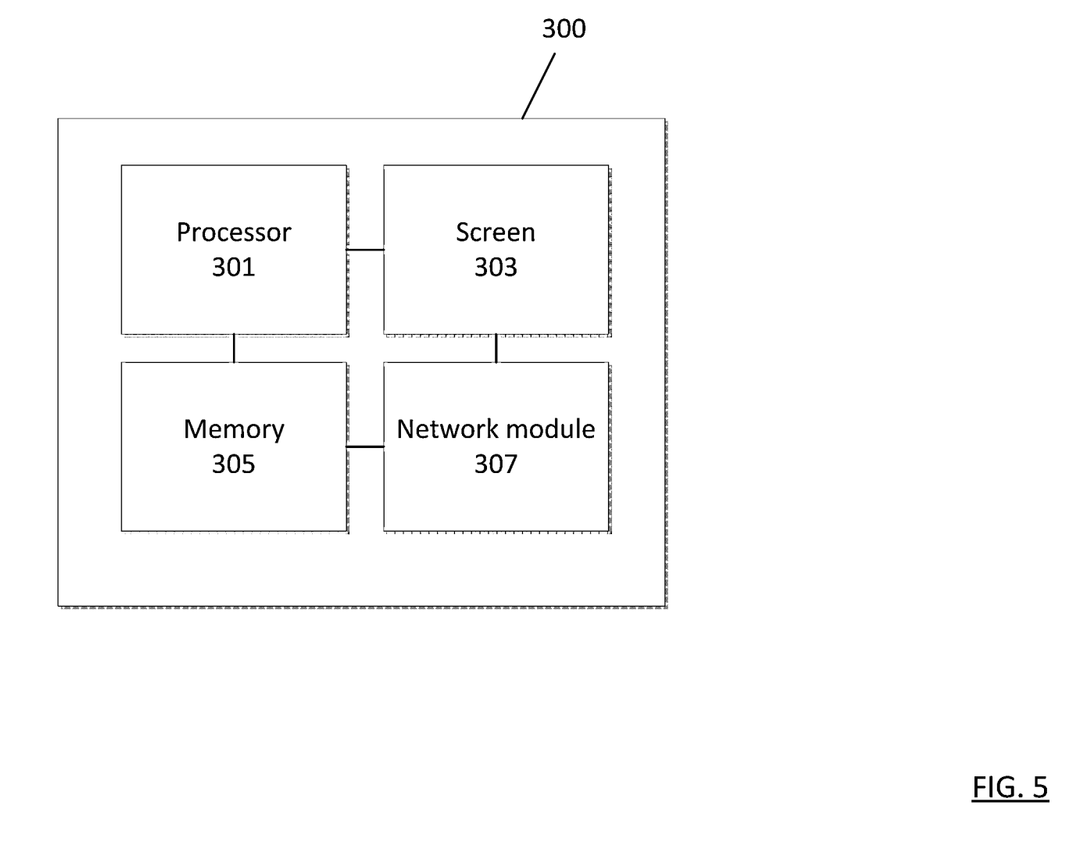
FIG. 5 is a hardware diagram of a mobile device, according to one embodiment of the present disclosure.

Referring to FIG. 5, the mobile device 300 can contain units for a processor 301, memory 305, screen 303, and network module 307, according to one exemplary embodiment. The mobile device 300 can take a myriad of forms, such as a phone, laptop, tablet, smart watch, smart glasses, or any other device with a processor, screen, memory, and network module.

The processor 301 may be based on a reduced instruction set (RISC) circuit architecture, Von Neumann architecture, Harvard architecture, or any other processing circuit architecture that is known. The processor 301 may also be implemented as a system on a chip, application specific integrated circuit (ASIC), field programmable gate array (FPGA), or with discrete logic circuit components. The processor 301 may also be implemented in software that is executed on processing circuitry having any of the architectures described above. The processor 301 can be connected to and control to the memory, network module, and screen. The processor 301 can be configured to run all or portions of method 600, 700, 800, and 900.

The memory 305 can be used to store instructions and other data (e.g. user profile information) needed by the processor 301 in order to carry out various tasks in accordance with exemplary aspects of the present disclosure. The memory 305 may include permanent instructions that do not require changes, such as lower-level routines. The memory 305 may include a combination of random access memory and erasable programmable read only memory (EPROM) in order to store programming instructions that may be periodically updated and data that may change periodically or frequently during as the processor 301 executes instructions.

The screen 303 can be used to output information to a user, as well as receive input from a user. For instance, the screen 303 can output icons to trigger VEP responses as the user views the icons. As another example, the screen 303 can be used to receive input from the user as they edit their user profile. The screen 303 can receive input via touch (capacitive or resistive), or have additional peripherals, such as a keyboard, trackpad, or mouse.

The mobile device 300 can also include a network module 307, such as an Intel Ethernet PRO network interface card from Intel Corporation of America, for interfacing with a network. As can be appreciated, the network can be a public network, such as the Internet, or a private network such as an LAN or WAN network, or any combination thereof and can also include PSTN or ISDN sub-networks. The network can be wired, such as via an Ethernet network, or can be wireless, such as via a cellular network including EDGE, 3G, 4G, and 5G wireless cellular systems. The wireless network can also be Wi-Fi, Bluetooth, NFC, radio frequency identification device, or any other wireless form of communication that is known. The network module 307 can be used to communicate with the vehicle 200.

Figure 6:
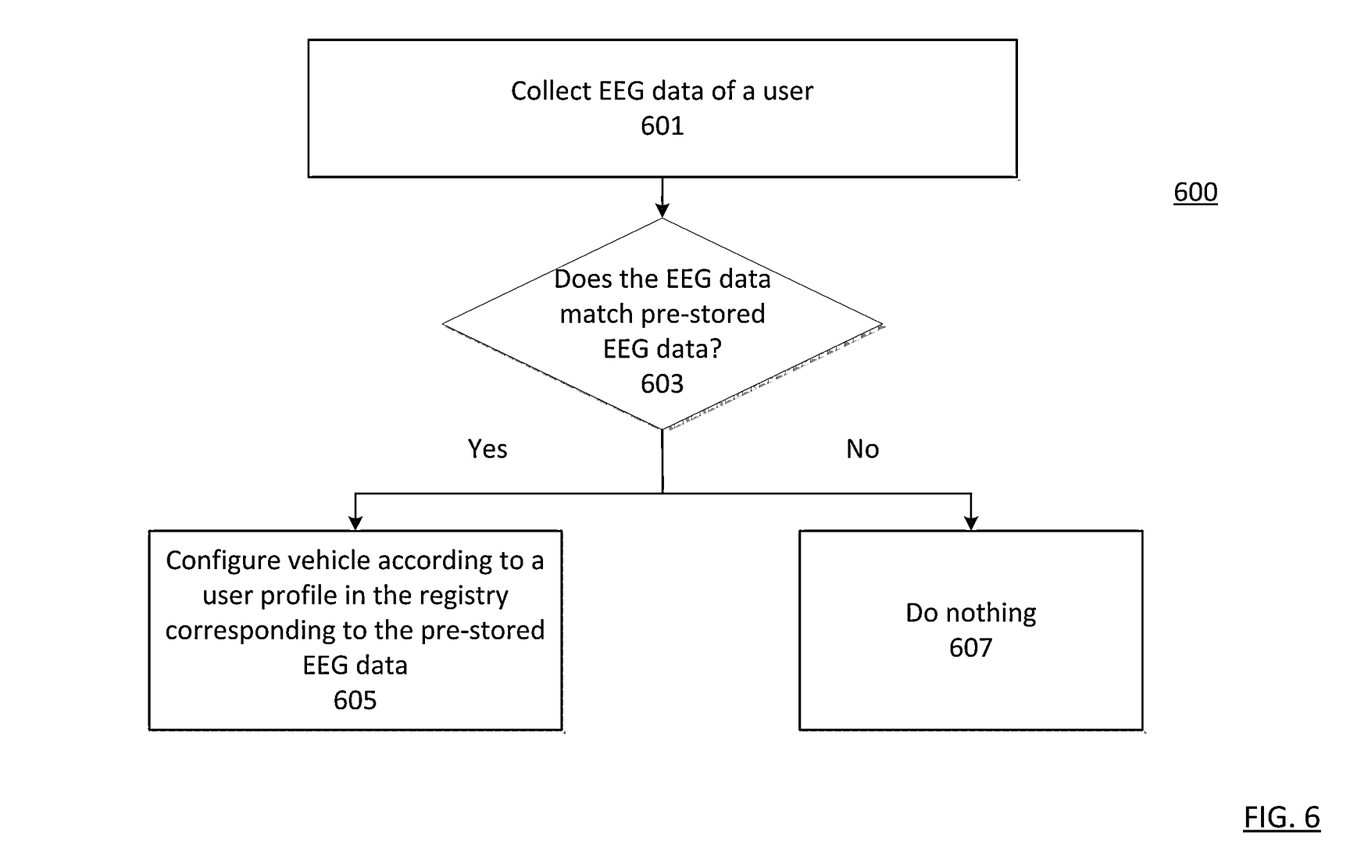
FIG. 6 is a first method for profile mapping, according to one embodiment of the present disclosure.

As can be appreciated by one of skill in the art, the present disclosure can be viewed as a method. FIG. 6 shows an algorithmic flowchart of a method 600 according to one exemplary embodiment. Step 601 is collecting EEG data of a user 101. The EEG data can be collected using contact-based or contactless brainwave detectors located inside or on an exterior of the vehicle 200. The EEG data can be collected from the user 101 as they think of a password, which will generate a unique EEG response. In one embodiment, the display module 219 can be used to visualize one or more icons for the user 101 to view, which will trigger the user's unique EEG response. The one or more icons can be oscillating at one or more various frequencies, which can trigger VEP responses in the brain.

Step 603 is determining if the EEG data collected from step 601 matches pre-stored EEG data in a registry. The registry includes user profiles and pre-stored EEG data corresponding to each of the user profiles.

If the answer to step 603 is no, step 607 is to do nothing. If the answer to step 603 is yes, step 605 is configuring the vehicle 200 according to a user profile in the registry corresponding to the pre-stored EEG data. The user profile can include information such as payment information, a desired destination, a routing preference, a desired temperature range, desired humidity range, desired light settings, desired audio settings, and desired seat settings for the vehicle 200. The registry and user profiles can be accessed via local hardware or network connection by the vehicle 200.

Figure 7:
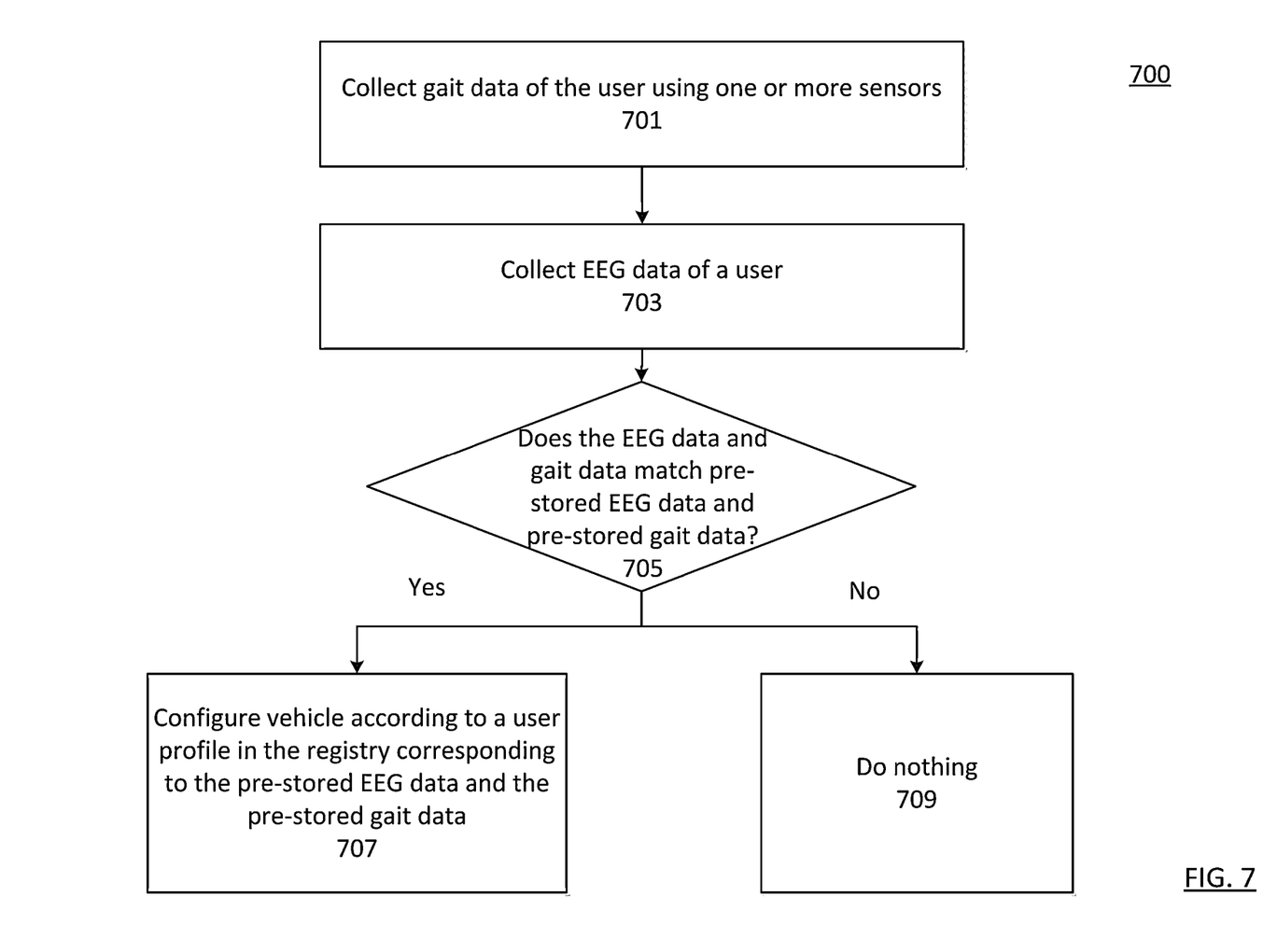
FIG. 7 is a second method for profile mapping, according to one embodiment of the present disclosure.

FIG. 7 shows another algorithmic flowchart of a method 700 according to one exemplary embodiment. Step 701 is collecting gait data of a user using one or more sensors. Gait data is related to the user's 101 gait. The one or more sensors can include a distance sensor (e.g. ultrasound, infrared, LIDAR) and imaging sensor (e.g. camera) located in or on an exterior of the vehicle 200 for analyzing the user's 101 gait as they walk towards the vehicle 200.

Step 703 is collecting EEG data of a user. Step 703 is the same as step 601 in method 600.

Step 705 is determining if the EEG data and gait data match pre-stored EEG data and pre-stored gait data. The registry includes user profiles and their corresponding pre-stored EEG data and pre-stored gait data. If both the EEG data and gait data match pre-stored EEG data and pre-stored gait data corresponding to a user profile, the answer to step 705 is yes, and step 707 is performed. If the answer to step 705 is no, step 709 is to do nothing.

Step 707 is configuring the vehicle 200 according to a user profile in the registry corresponding to the pre-stored EEG data and the pre-stored gait data. The user profile can include information such as payment information, a desired destination, a routing preference, a desired temperature range, desired humidity range, desired light settings, desired audio settings, and desired seat settings for the vehicle 200. The registry and user profiles can be accessed via local hardware or network connection by the vehicle 200.

Figure 8:
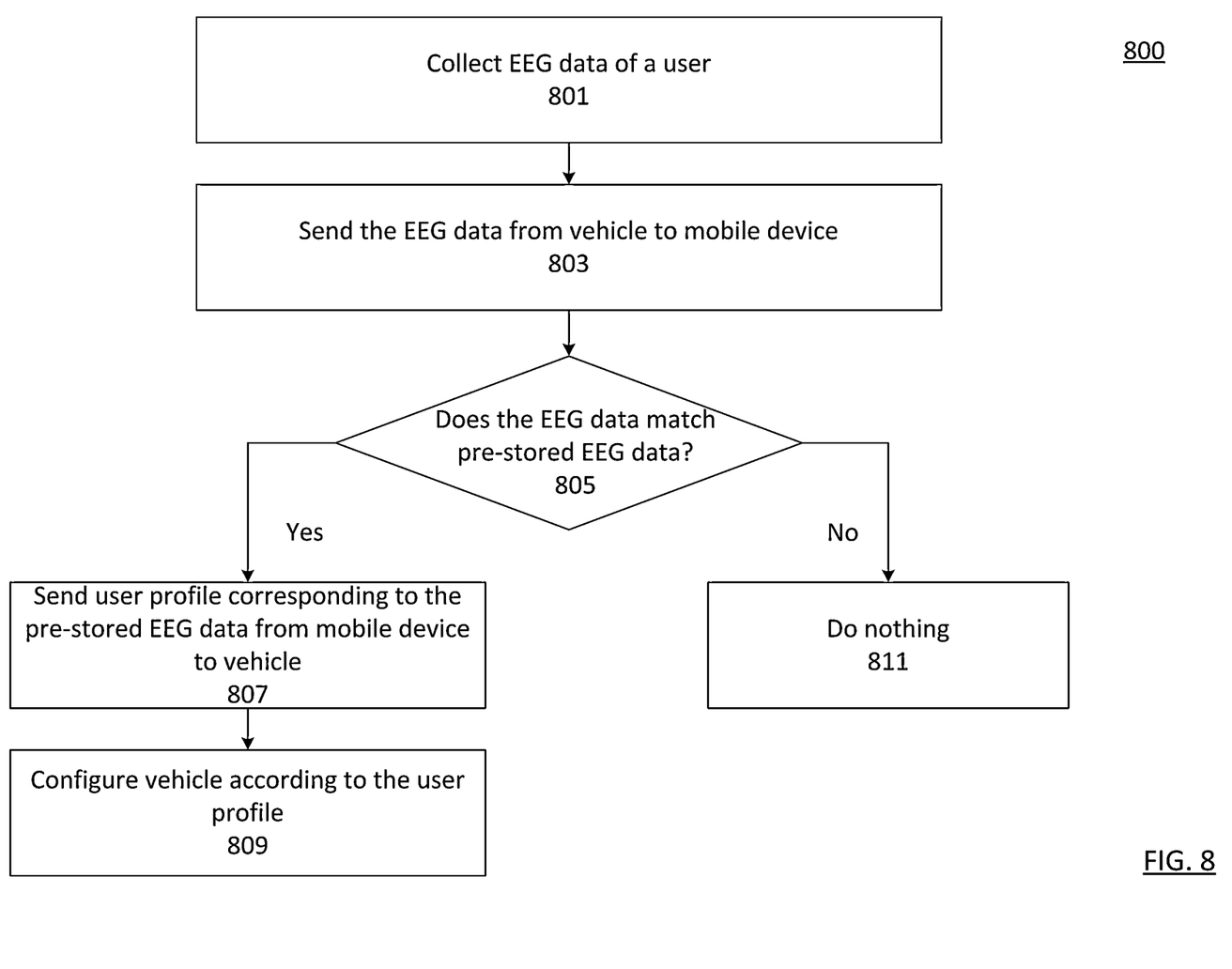
FIG. 8 is a third method for profile mapping, according to one embodiment of the present disclosure.

FIG. 8 shows another algorithmic flowchart of a method 800 according to one exemplary embodiment. Step 801 is collecting EEG data of a user 101. Step 801 is the same as step 601 in method 600.

Step 803 is sending the EEG data collected in step 801 from the vehicle 200 to a mobile device 300. The mobile device 300 has access to the registry and user profile, while the vehicle 200 does not. The registry can include one or more user profiles for one user or multiple users. The EEG data can be sent using any technique known by those of skill in the art, such as via Bluetooth or NFC.

Step 805 determining if the EEG data match pre-stored EEG data. Step 805 is performed by the mobile device 300. If the EEG data does not match any pre-stored EEG data, step 811 is to do nothing.

If the answer the step 805 is yes, step 807 is to send the user profile corresponding to the pre-stored EEG data from the mobile device 300 to the vehicle 200. The user profile can be sent using any technique known by those of skill in the art, such as via Bluetooth or NFC.

Step 809 is to configure the vehicle 200 according to the user profile sent during step 807. Step 807 is the same as step 605 of method 600.

Figure 9:
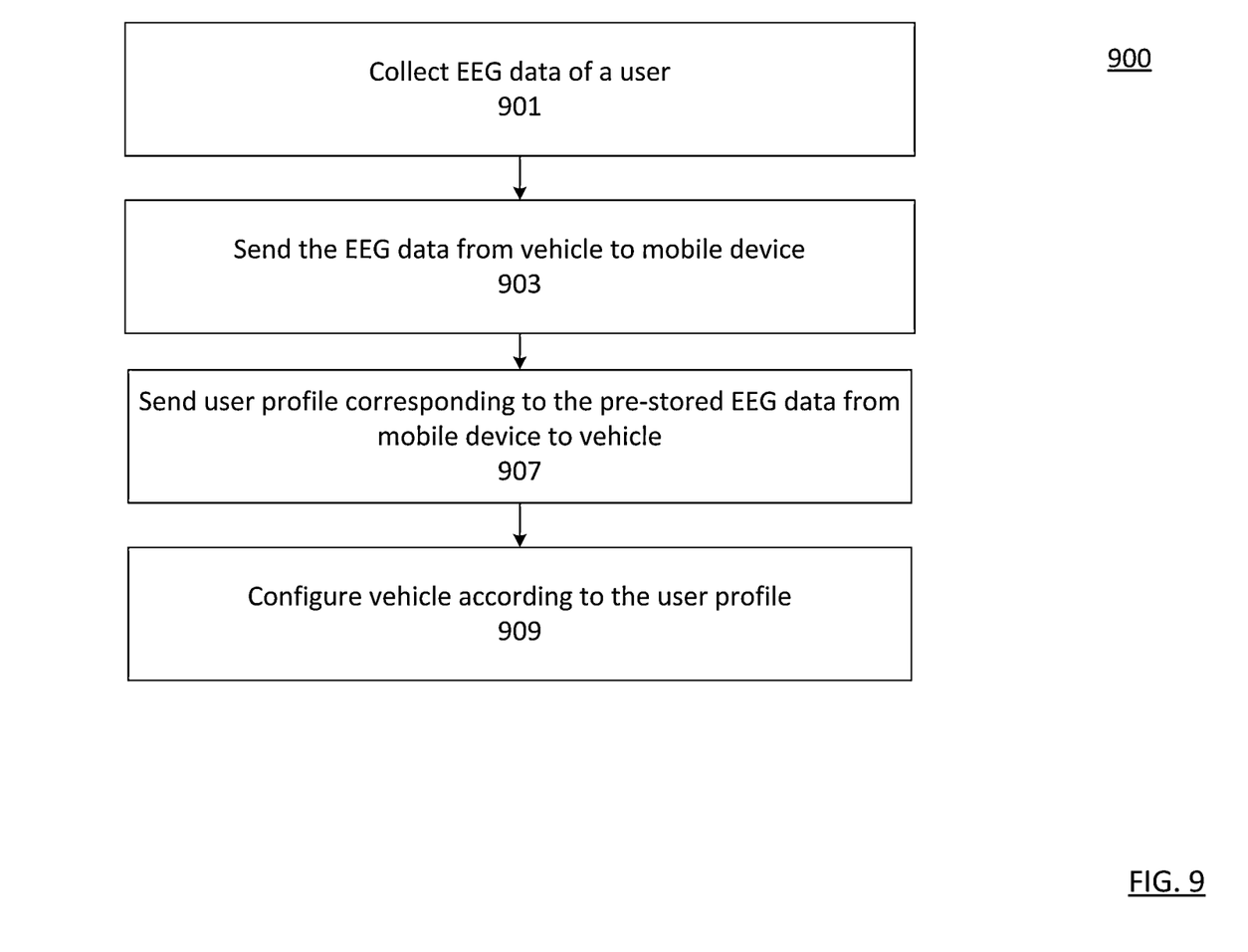
FIG. 9 is a fourth method for profile mapping, according to one embodiment of the present disclosure.

FIG. 9 shows another algorithmic flowchart of a method 900 according to one exemplary embodiment. Step 901 is collecting EEG data of a user, followed by sending the EEG data from a vehicle to a mobile device in step 903, sending a user profile corresponding to the pre-stored EEG data from the mobile device to the vehicle in step 907, and configuring the vehicle according to the user profile in step 909.

Method 900 is nearly identical to method 800, where step 901 is the same as 801, step 903 is the same as 803, step 907 is the same as step 807, and step 909 is the same as step 809. The difference between method 800 and 900 is that steps 805 and 811 from method 800 are removed in method 900. In method 900, the acquired EEG signal is expected to always match the pre-registered profile of the user, and in such a case, steps 805 and 811 are not necessary.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Embodiments of the present disclosure may also be as set forth in the following parentheticals.

(1) A vehicle system comprising processing circuitry configured to collect electroencephalogram (EEG) data, using a brainwave detector, of a user, and in a case that the EEG data matches pre-stored EEG data in a registry, configure the vehicle according to a user profile in the registry corresponding to the pre-stored EEG data.

(2) The system of (1), wherein the processing circuitry is further configured to transmit the EEG data to a mobile device, the mobile device having access to the registry and the user profile, and in the case that the EEG data of the user matches the pre-stored EEG data in the registry, receive the user profile corresponding to the pre-stored EEG data from the mobile device.

(3) The system of any (1) to (2), wherein the processing circuitry is further configured to display one or more icons to the user to generate the EEG data.

(4) The system of any (1) to (3), wherein the brainwave detector is a contactless brainwave detector.

(5) The system of any (1) to (4), wherein the user profile include at least one of a desired destination, a routing preference, a desired temperature range, desired humidity range, desired light settings, desired audio settings, and desired seat settings for the vehicle.

(6) The system of any (1) to (5), wherein the user profile includes payment information of the user.

(7) The system of any (1) to (6), wherein the brainwave detector is inside the vehicle.

(8) The system of any (1) to (7), wherein the brainwave detector is disposed on an exterior of the vehicle.

(9) A vehicle system comprising, processing circuitry configured to collect EEG data, using a brainwave detector, of a user, collect secondary biometric data of the user using one or more sensors, and in a case that at least one of the EEG data and the secondary biometric data match pre-stored EEG data and pre-stored secondary biometric data in a registry, configure the vehicle according to a user profile in the registry corresponding to the pre-stored EEG data and the pre-stored secondary biometric data.

(10) The system of (9), wherein the secondary biometric data is gait data of the user's gait.

(11) The system of any (9) to (10), wherein the brainwave detector is a contactless brainwave detector.

(12) A method comprising: collecting EEG data, using a brainwave detector, of a user; and in a case that the EEG data matches pre-stored EEG data in a registry, configuring a vehicle according to a user profile in the registry corresponding to the pre-stored EEG data.

(13) The method of any (12), further comprising: transmitting the EEG data from the vehicle to a mobile device, the mobile device having access to the registry and the user profile, and in the case that the EEG data of the user matches the pre-stored EEG data in the registry, transmitting the user profile corresponding to the pre-stored EEG data from the mobile device to the vehicle.

(14) The method of any (12) to (13), further comprising: displaying one or more icons to the user to generate the EEG data.

(15) The method of any (12) to (14), further comprising: collecting secondary biometric data of the user.

(16) The method of any (12) to (15), wherein the brainwave detector is a contactless brainwave detector.

(17) The method of any (12) to (16), wherein the user profile include at least one of a desired destination, a routing preference, a desired temperature range, desired humidity range, desired light settings, desired audio settings, and desired seat settings for the vehicle.

(18) The method of any (12) to (17), wherein the user profile includes payment information of the user.

(19) The method of any (12) to (18), wherein the brainwave detector is inside the vehicle.

(20) The method of any (12) to (19), wherein the brainwave detector is disposed on an exterior of the vehicle.

The invention claimed is:

1. A vehicle system comprising:
    processing circuitry configured to:
        display one or more of an image, a sign, a graphic, and an icon to a user,
        collect electroencephalogram (EEG) data, using a brainwave detector, of a brainwave response of the user seeing the one or more the image, the sign, the graphic, and the icon, and
        in a case that the EEG data matches pre-stored EEG data in a registry, configure a vehicle according to a user profile in the registry corresponding to the pre-stored EEG data,
    wherein the pre-stored EEG data in the registry is data of a brainwave response of the user seeing the one or more the image, the sign, the graphic, and the icon at a previous point in time.

2. The system of claim 1, wherein the processing circuitry is further configured to:
    transmit the EEG data to a mobile device, the mobile device having access to the registry and the user profile, and
    in the case that the EEG data of the user matches the pre-stored EEG data in the registry, receive the user profile corresponding to the pre-stored EEG data from the mobile device.

3. The system of claim 1, wherein the brainwave detector is a contactless brainwave detector.

4. The system of claim 1, wherein the user profile includes at least one of a desired destination, a routing preference, a desired temperature range, desired humidity range, desired light settings, desired audio settings, and desired seat settings for the vehicle.

5. The system of claim 1, wherein the user profile includes payment information of the user.

6. The system of claim 1, wherein the brainwave detector is inside the vehicle.

7. The system of claim 1, further comprising a display disposed on an exterior of the vehicle, wherein the brainwave detector is disposed on the exterior of the vehicle such that the EEG data of the brainwave response of the user seeing the one or more the image, the sign, the graphic, and the icon is collected while the user is outside of the vehicle.

8. The system of claim 1, wherein
    the one or more the image, the sign, the graphic, and the icon includes a plurality of icons, and
    the processing circuitry is further configured to display the plurality of icons in a series.

9. The system of claim 8, wherein the collected EEG data includes a brainwave response of the user looking at the plurality of icons in a secret sequence.

10. A vehicle system comprising,
    processing circuitry configured to:
        display one or more of an image, a sign, a graphic, and an icon to a user,
        collect electroencephalogram (EEG data), using a brainwave detector, of a brainwave response of the user seeing the one or more the image, the sign, the graphic, and the icon,
        collect secondary biometric data of the user using one or more sensors, and
        in a case that at least one of the EEG data and the secondary biometric data match pre-stored EEG data and pre-stored secondary biometric data in a registry, configure vehicle according to a user profile in the registry corresponding to the pre-stored EEG data and the pre-stored secondary biometric data,
    wherein the pre-stored EEG data in the registry is data of a brainwave response of the user seeing the one or more the image, the sign, the graphic, and the icon at a previous point in time.

11. The system of claim 10, wherein the secondary biometric data is gait data of a gait of the user.

12. The system of claim 10, wherein the brainwave detector is a contactless brainwave detector.

13. A method comprising:
    display one or more of an image, a sign, a graphic, and an icon to a user;
    collecting electroencephalogram (EEG) data, using a brainwave detector, of a brainwave response of the user seeing the one or more the image, the sign, the graphic, and the icon; and
    in a case that the EEG data matches pre-stored EEG data in a registry, configuring a vehicle according to a user profile in the registry corresponding to the pre-stored EEG data,
    wherein the pre-stored EEG data in the registry is data of a brainwave response of the user seeing the one or more the image, the sign, the graphic, and the icon at a previous point in time.

14. The method of claim 13, further comprising:
    transmitting the EEG data from the vehicle to a mobile device, the mobile device having access to the registry and the user profile, and
    in the case that the EEG data of the user matches the pre-stored EEG data in the registry, transmitting the user profile corresponding to the pre-stored EEG data from the mobile device to the vehicle.

15. The method of claim 13, further comprising collecting secondary biometric data of the user.

16. The method of claim 13, wherein the brainwave detector is a contactless brainwave detector.

17. The method of claim 13, wherein the user profile includes at least one of a desired destination, a routing preference, a desired temperature range, desired humidity range, desired light settings, desired audio settings, and desired seat settings for the vehicle.

18. The method of claim 13, wherein the user profile includes payment information of the user.

19. The method of claim 13, wherein the brainwave detector is inside the vehicle.

20. The method of claim 13, wherein a display and the brainwave detector are disposed on an exterior of the vehicle such that the EEG data of the brainwave response of the user seeing the one or more the image, the sign, the graphic, and the icon is collected while the user is outside of the vehicle.

* * * * *